US008026494B2

(12) United States Patent
Kimura

(10) Patent No.: US 8,026,494 B2
(45) Date of Patent: *Sep. 27, 2011

(54) FLOURESCENCE DETECTING METHOD AND FLUORESCENCE DETECTING APPARATUS

(75) Inventor: Toshihito Kimura, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 221 days.

This patent is subject to a terminal disclaimer.

(21) Appl. No.: 12/415,148

(22) Filed: Mar. 31, 2009

(65) Prior Publication Data

US 2009/0242802 A1    Oct. 1, 2009

(30) Foreign Application Priority Data

Mar. 31, 2008    (JP) ................ 2008-089503

(51) Int. Cl.
G01N 21/64    (2006.01)
(52) U.S. Cl. .................... 250/458.1
(58) Field of Classification Search ........... 250/458.1
See application file for complete search history.

(56) References Cited

U.S. PATENT DOCUMENTS

| | | | | |
|---|---|---|---|---|
| 5,341,215 | A * | 8/1994 | Seher | 356/445 |
| 6,268,125 | B1 * | 7/2001 | Perkins | 435/5 |
| 7,154,598 | B2 * | 12/2006 | Montagu et al. | 356/244 |
| 2009/0230308 | A1 * | 9/2009 | Kimura | 250/363.01 |

OTHER PUBLICATIONS

Yeechi Chen, Keiko Munechika, and David S. Ginger, "Dependence of Fluorescence Intensity on the Spectral Overlap between Fluorophores and Plasmon Resonant Single Silver Nanoparticles." Nano Lett. 2007, vol. 7, No. 3, pp. 690-696 <doi:10.1021/nl062795z> Publication Date (Web): Feb. 22, 2007. Downloaded Dec. 29, 2010.*

Margarida M. L. M. Vareiro, et al., "Surface Plasmon Fluorescence Measurements of Human Chorionic Gonadotrophin: Role of Antibody Orientation in Obtaining Enhanced Sensitivity and Limit of Detection", Analytical Chemistry, 2005, pp. 2426-2431, vol. 77, No. 8.

* cited by examiner

*Primary Examiner* — Constantine Hannaher
(74) *Attorney, Agent, or Firm* — Sughrue Mion, PLLC

(57) ABSTRACT

An excitation light beam of a wavelength that excites fluorescent labels and a reference light beam having a wavelength longer than the excitation light beam are irradiated through a dielectric block toward an interface between the dielectric block and a metal film, to cause a first electric field enhancing field and a second electric field enhancing field on the upper surface of the metal film, in fluorescence detection that utilizes surface plasmon. The intensity of scattered light of the second electric field enhancing field, which is substantially proportionate to the intensity of the second electric field enhancing field, is employed to normalize and correct the intensity of fluorescence emitted by fluorescent labels with respect to the intensity of the first electric field enhancing field, based on the relationship between the intensities of the first and second electric field enhancing fields.

5 Claims, 5 Drawing Sheets

FLUORESCENCE DETECTING METHOD AND FLUORESCENCE DETECTING APPARATUS

BACKGROUND OF THE INVENTION

1. Field of the Invention

The present invention is related to a fluorescence detecting method and a fluorescence detecting apparatus that utilize surface plasmon. More specifically, the present invention is related to a fluorescence detecting method and a fluorescence detecting apparatus that utilizes a correcting mechanism to correct detected intensities of fluorescence.

2. Description of the Related Art

Conventionally, detecting methods that utilize totally reflected illumination are being focused on, in biological measurements for detecting proteins, DNA, and the like. These detection methods detect the presence or the amount of a detection target substance, by analyzing optical interactions such as scattering, absorption, and light emission, between light that leaks out when a measuring light beam is totally reflected at an interface between materials having different refractive indices, that is, evanescent waves, and the detection target substance, which is included in a sample, or labels attached to the detection target substance.

An example of such a detecting method is a fluorescence detecting method that utilizes fluorescent labels (refer to Margarida M. L. M. Vareiro et al., "Surface Plasmon Fluorescence Measurements of Human Chorionic Gonadotrophin: Role of Antibody Orientation in Obtaining Enhanced Sensitivity and Limit of Detection", Analytical Chemistry, Vol. 77, No. 8, pp. 2426-2431, 2005.)

With recent advances in the performance of photodetectors, such as cooled CCD's, fluorometry has become indispensable in biological research. In addition, fluorescent pigments having fluorescence quantum yields that exceed 0.2, which is the standard for practical use, such as FITC (fluorescence: 525 nm, fluorescence quantum yield: 0.6) and Cy5 (fluorescence: 680 nm, fluorescence quantum yield: 0.3) have been developed as fluorescent labeling materials and are being widely used. Further, high sensitivity detection on the order of 1 pM and less is being realized, by amplifying fluorescence signals employing electric field enhancing fields due to surface plasmon.

The principles of the aforementioned fluorescence detecting method will be explained with reference to FIG. 7.

FIG. 7 is a conceptual diagram that illustrates a fluorescence detecting apparatus. For the sake of convenience in the explanation, the dimensions of each component are not drawn to actual scale.

The fluorescence detecting apparatus illustrated in FIG. 7 is equipped with: a sensor chip 10 constituted by a dielectric plate 11 and a metal film 12 provided at a predetermined region on one surface of the dielectric plate; an excitation light outputting optical system 20 that outputs an excitation light beam $L_0$ at an incident angle that satisfies conditions for total reflection at the interface between the dielectric plate 11 and the metal film 12 from the side of the sensor chip 10 opposite the surface on which the metal film 12 is formed; and a photodetector 30 that detects fluorescence $L_0$ generated by fluorescent labels F, which are attached to a detection target substance A, in the case that the detection target substance A having the fluorescent labels F attached thereto are present in a sample S in contact with the metal film 12.

In this fluorescence detecting apparatus, the excitation light beam $L_0$ is output from the excitation light outputting optical system 20 and enters the interface between the dielectric plate 11 and the metal film 12 at a specific incident angle greater than or equal to a total reflection angle. Thereby, evanescent waves leak into the sample S on the metal film 12, and surface plasmon within the metal film 12 are excited by the evanescent waves. The evanescent waves and the surface plasmon cause an electric field enhancing field Ew that exhibits an electric field enhancing effect to be formed locally on the surface of the metal film 12.

A case will be considered in which antigens A are detected from within a sample S that includes the antigens A as a detection target substance. The metal film 12 is modified with primary antibodies B1 that specifically bind with the antigens A. The sample S is caused to flow into a sample holding section 13, and then secondary antibodies B2, which are modified with fluorescent labels F and that also specifically bind with the antigens A, are caused to flow into the sample holding section 13. At this time, the fluorescent labels F are immobilized to the metal film 12 via the specific bonds of the primary antibodies B1, the antigens A, and the secondary antibodies B2.

In the case described above, the fluorescent labels F are present within the electric field enhancing field Ew, and the fluorescent labels F are excited and caused to emit fluorescence Lf. Accordingly, the antigens A can be detected by detecting the fluorescence Lf. Note that the presence of the fluorescent labels F is actually directly confirmed by the detection of fluorescence. However, it is considered that the fluorescent labels F would not be immobilized onto the metal film 12 unless the antigens A are present. Therefore, the binding between the secondary antibodies B2 and the antigens A, that is, the presence of the antigens A, is indirectly confirmed by confirming the presence of the fluorescent labels F.

However, in the aforementioned fluorescent detecting method, there are many factors that contribute to fluctuations in the intensity of the electric field enhancing field generated by surface plasmon. Therefore, it is difficult to completely uniformize all of the factors for each measurement. This causes a problem that detected intensities of fluorescence fluctuate, and that reproducibility is poor, even if the amounts of detection target substances within samples are the same. These factors include: margins of error in the shapes and settings of sensor chips; shifting in the incident angle of excitation light beams caused by human error such as margins of errors in sensing and margins of error in setup of the optical system; and shifting in surface plasmon generating conditions due to physical factors such as the refractive indices of samples, the refractive indices of the sensor chips, irregularities on the surfaces of the sensor chips, the thicknesses of the metal films, and the densities of the metal films. In addition, changes in environmental temperatures during measurement may also lead to shifting in the aforementioned conditions, and therefore must be considered as well.

Variations in the aforementioned factors can be suppressed by selecting or exchanging components for optimal components for each measurement. However, extreme amounts of trouble and cost will be incurred if variations in all of the factors are suppressed by selecting or exchanging components.

SUMMARY OF THE INVENTION

The present invention has been developed in view of the aforementioned problem. It is an object of the present invention to provide a fluorescence detecting method and a fluorescence detecting apparatus that can realize measurements having reproducibility, in which fluctuations in intensities of electric field enhancing fields that occur at each measurement are suppressed, simply and at low cost.

A fluorescence detecting method of the present invention is characterized by comprising the steps of:

preparing a dielectric plate, and a metal film which is provided at a predetermined region on one surface of the dielectric plate, onto which a sample that includes a detection target substance and fluorescent labels is supplied;

irradiating an excitation light beam through the dielectric plate such that it enters the interface between the dielectric plate and the metal film, to cause a first electric field enhancing field to be generated on the surface of the metal film;

detecting fluorescence emitted by the fluorescent labels due to excitation by the first electric field enhancing field with a first photodetector;

detecting the amount of the detection target substance based on the intensity of fluorescence detected by the first photodetector;

irradiating a reference light beam having a longer wavelength than the excitation light beam through the dielectric plate, to cause a second electric field enhancing field to be generated on the surface of the metal film at the same location as the first electric field enhancing field;

detecting scattered light of the second electric field enhancing field, which is substantially proportionate to the intensity of the second electric field enhancing field, with a second photodetector;

estimating the intensity of the first electric field enhancing field based on the relationship between the intensity of the first electric field enhancing field and the intensity of the second electric field enhancing field, using the intensity of the scattered light detected by the second photodetector; and normalizing and correcting the intensity of fluorescence with respect to the intensity of the first electric field enhancing field.

In the fluorescence detecting method of the present invention, it is preferable for the first photodetector to also function as the second photodetector; and for the excitation light beam and the reference light beam to be irradiated separately. Alternatively, the excitation light beam and the reference light beam may be irradiated simultaneously.

Here, the term "electric field enhancing field" refers to a local region on the upper surface of the metal film that exhibits an enhancing effect of electric fields, generated due to the evanescent waves which are generated by irradiating the excitation light beam onto the interface between the dielectric plate and the metal film such that conditions for total reflection are satisfied at the interface, and due to surface plasmon which are induced by the evanescent waves and generated within the metal film.

The phrase "intensity of fluorescence being normalized . . . with respect to the intensity of the electric field enhancing field" means that an intensity of fluorescence is determined to be a reference with respect to an arbitrary intensity of the electric field enhancing field, and relatively estimating actually measured intensities of fluorescence based on the reference intensity of fluorescence.

A fluorescence detecting apparatus of the present invention is a fluorescence detecting apparatus for detecting the amount of a detection target substance, characterized by comprising:

a dielectric plate;

a metal film which is provided at a predetermined region on one surface of the dielectric plate, onto which a sample that includes the detection target substance and fluorescent labels is supplied;

a light source for irradiating an excitation light beam through the dielectric plate such that it enters the interface between the dielectric plate and the metal film, to cause an electric field enhancing field to be generated on the surface of the metal film;

a first photodetector for detecting the intensity of fluorescence generated by the excitation effect of the electric field enhancing field;

a light source for irradiating a reference light beam having a longer wavelength than the excitation light beam through the dielectric plate, to cause a second electric field enhancing field to be generated on the surface of the metal film at the same location as the first electric field enhancing field;

a second photodetector for detecting scattered light of the second electric field enhancing field, which is substantially proportionate to the intensity of the second electric field enhancing field; and a correcting mechanism, for normalizing and correcting the intensity of fluorescence with respect to the intensity of the first electric field enhancing field based on the relationship between the intensity of the first electric field enhancing field and the intensity of the second electric field enhancing field, using the intensity of the scattered light detected by the second photodetector;

the amount of the detection target substance being detected based on the intensity of fluorescence detected by the first photodetector, which has been corrected by the correcting mechanism.

In the fluorescence detecting apparatus of the present invention, the first photodetector may also function as the second photodetector.

Note that in the fluorescence detecting method and the fluorescence detecting apparatus of the present invention, the phrase "detecting the amount of a detection target substance" refers not only to detecting quantitative amounts of the detection target substance, but qualitatively detecting whether the detection target substance is present. The phrase also refers to detection of degrees of activity of the detection target substance.

In the fluorescence detecting method and the fluorescence detecting apparatus of the present invention, the intensity of fluorescence detected in each measurement is corrected based on the intensity of the scattered light of the second electric field enhancing field, which is generated by irradiation of the reference light beam having a longer wavelength than the excitation light beam. The intensity of fluorescence and the intensity of scattered light are both dependent on the generated state of the first electric field enhancing field and the second electric field enhancing field. In addition, the generated state of the electric field enhancing field is dependent on the measurement environment. Accordingly, the scattered light, the intensity of which is substantially proportionate to the intensity of the first electric field enhancing field and the second electric field enhancing field, is employed as an index of the generated state of the first electric field enhancing field and the second electric field enhancing field. Thereby, the intensity of the first electric field enhancing field can be estimated from the relationships between the intensity of the first electric field enhancing field and the intensity of the second electric field enhancing field. Thereby, it becomes possible to normalize and correct the intensity of fluorescence with respect to the intensity of the first electric field enhancing field.

As described above, correction suited to conditions can be performed for each measurement, and the factors that contribute to fluctuations in the intensity of the electric field enhancing effect that occur during each measurement can be suppressed. Accordingly, measurements having reproducibility can be realized simply and at low cost, without selecting or exchanging components to be optimal for each measurement.

BEST MODE FOR CARRYING OUT THE INVENTION

Hereinafter, embodiments of the present invention will be described with reference to the attached drawings. However, the present invention is not limited to the embodiments to be described below.
[Fluorescence Detecting Method and Fluorescence Detecting Apparatus]

First Embodiment

Figure 1:
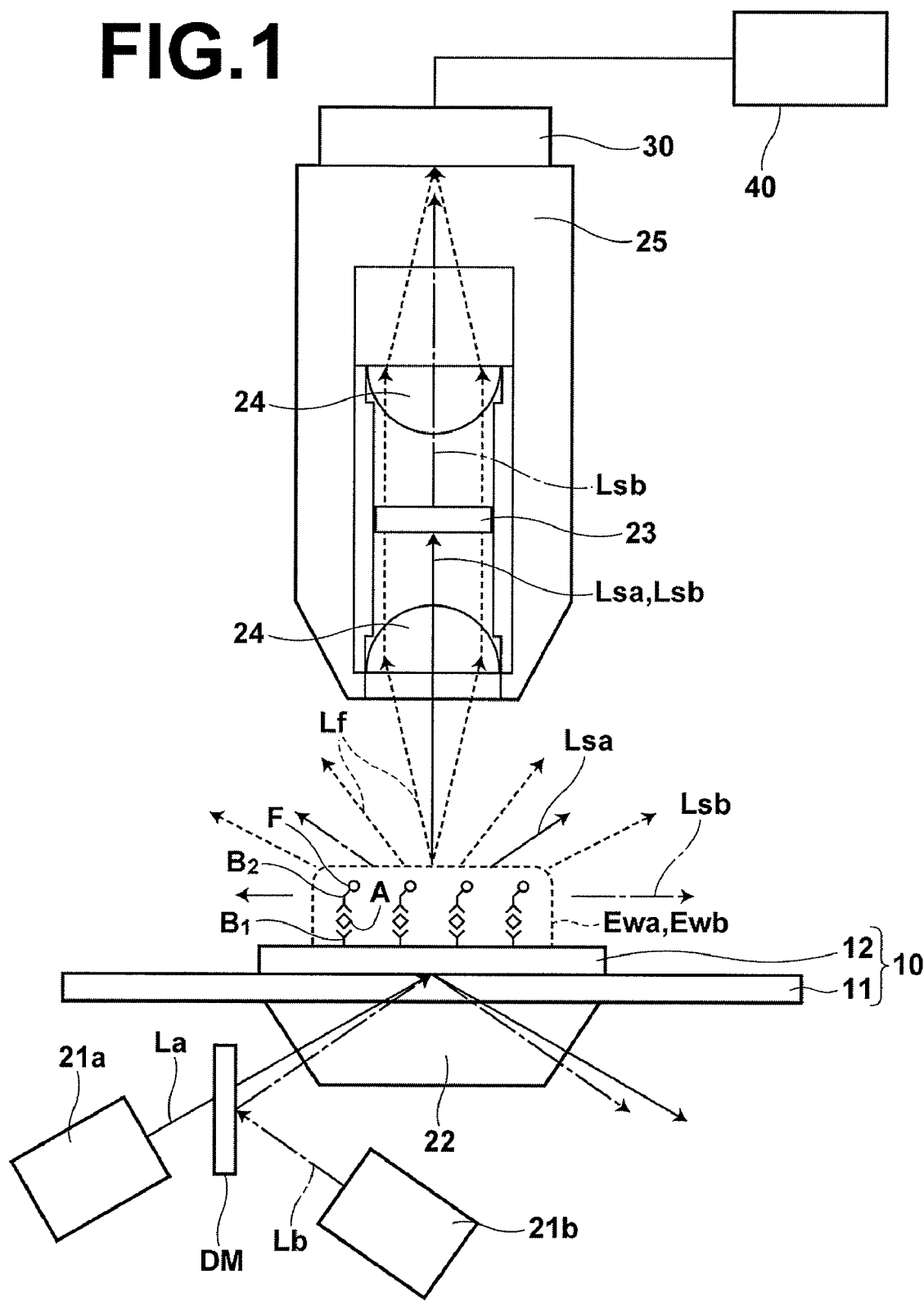
FIG. 1 is a schematic sectional view that illustrates a fluorescence detecting apparatus according to a first embodiment of the present invention.

FIG. 1 is a schematic diagram that illustrates a fluorescence detecting apparatus according to a first embodiment of the present invention.

As illustrated in FIG. 1, the fluorescence detecting apparatus is equipped with: a sensor chip 10 constituted by a dielectric plate 11 and a metal film 12; a light source 21a that emits an excitation light beam La having a wavelength of 657 nm that excites fluorescent labels F; a light source 21b that emits a reference light beam Lb having a wavelength of 670 nm, which is longer than the wavelength of the excitation light beam La; a prism 22, on which the sensor chip 10 is placed; an optical system DM for guiding the reference light beam Lb such that it passes through the prism 22 and enters the interface between the dielectric plate 11 and the metal film 12 such that a second electric field enhancing field Ewb is generated on the metal film 12; a photodetector 30 for detecting fluorescence Lf emitted by the fluorescent labels F which are supplied onto the sensor chip 10; two planoconvex lenses 24 which are arranged so as to guide the fluorescence Lf to the photodetector 30; an optical filter 23 provided between the two planoconvex lenses 24, for cutting off scattered light Lsa of a first electric field enhancing field Ewa while transmitting the fluorescence Lf and scattered light Lsb of the second electric field enhancing field; and a correction calculating mechanism 40 connected to the photodetector 30. Here, the light source 21a is provided toward the side of the prism 22 from the dielectric plate 11, such that the first electric field enhancing field Ewa is generated on the sensor chip 10. The fluorescent labels F are immobilized onto the metal film 12 via primary antibodies B1, antigens A and secondary antibodies B2. In addition, reference numeral 25 in FIG. 1 denotes an optical system holding portion, in which the two planoconvex lenses 24 and the optical filter 23 are contained, and to which the first photodetector 30a is mounted.

The sensor chip 10 is not particularly limited, and is constituted by the metal film 12, which is formed on a predetermined region of a surface of the dielectric plate 11.

The dielectric plate 11 may be formed by transparent materials such as transparent resins and glass. It is desirable for the dielectric plate 11 to be formed by resin. In the case that the dielectric plate 11 is formed by resin, polymethyl methacrylate (PMMA), polycarbonate (PC), and non crystalline polyolefin (APO) that includes cycloolefin may be favorably employed.

The metal film 12 may be formed by known vapor deposition methods. The thickness of the metal film 12 is preferably set appropriately according to the material of the metal film 12 and such that surface plasmon is strongly excited by the wavelength of the excitation light beam $L_0$. For example, in the case that a laser beam having a central wavelength of 780 nm is employed as the excitation light beam La and a gold (Au) film is employed as the metal film 12, a favorable thickness of the metal film 12 is 50 nm±5 nm. Note that it is preferable for the metal film 12 to have at least one metal selected from among a group consisting of Au, Ag, Cu, Pt, Ni, Ti, and alloys thereof as a main component.

Note that a sample holding section for holding liquid samples may be provided on the sensor chip 10, and the sensor chip 10 and the sample holding section may constitute a box shaped cell, which is capable of holding liquid samples. On the other hand, in cases that extremely small amounts of liquid samples, to a degree which can be held on the sensor chip 10 by surface tension, are to be measured, the sensor chip 10 may not be provided with the sample holding section.

The prism 22 guides the excitation light beam La and the reference light beam Lb such that the excitation light beam La and the reference light beam Lb are totally reflected at the interface between the dielectric plate 11 and the metal film 12. Note that the prism 22 and the dielectric plate 11 are in contact via a refractive index matching oil.

The light source 21a is not particularly limited, and may be a laser light source. The type of light source to be employed as the light source 21a may be appropriately selected according to detection conditions. As described previously, the light source 21a is arranged such that the excitation light beam La output thereby enters the interface between the dielectric plate 11 and the metal film 12 at a specific angle that causes total reflection at the interface, and such that surface plasmon resonance occurs at the metal film 12. Further, a light guiding member may be provided between the light source 21 and the prism 22 as necessary. Note that it is preferable for the excitation light beam La to enter the interface in a P polarized state, such that surface plasmon can be induced.

The light source 21b is not particularly limited, and may be a laser light source. The type of light source to be employed as the light source 21b may be appropriately selected according to detection conditions. The light source 21b may be provided such that the reference light beam Lb output thereby enters the interface between the dielectric plate 11 and the metal film 12 via the optical system DM such as a dichroic mirror at a specific angle that causes total reflection at the interface, and such that surface plasmon resonance occurs at the metal film 12, in a manner similar to the light source 21a. Further, a light guiding member may be provided between the light source 21b and the prism 22 as necessary. Note that it is preferable for the excitation light beam Lb to enter the interface in a P polarized state, such that surface plasmon can be induced.

The excitation light beam La and the reference light beam Lb are not particularly limited, and may be a single wavelength light beam emitted from a laser light source or the like, or a broad spectrum light beam emitted from a white light source. The type of light beam to be employed as the excitation light beam La may be appropriately selected according to the type of fluorescent labels F which is employed. Meanwhile, it is preferable for the reference light beam Lb to have a longer wavelength than the excitation light beam La, such that the reference light beam Lb can be transmitted through the optical filter 23 that separates the scattered light Lsa and the fluorescence Lf. It is not necessary to take the fact that the spectra of the fluorescence Lf and the scattered light Lsb overlap in the first embodiment. Therefore, it is preferable for the wavelength of the reference light beam Lb to be that which causes the scattered light Lsb to be transmitted through the optical filter 23 and detectable, while being close to the wavelength of the excitation light beam La. By adopting this configuration, data for correction can be obtained at conditions that approximate actual measurement conditions.

The photodetector 30 is not limited, as long as it is capable of quantitatively detecting the fluorescence Lf emitted by the fluorescent labels F included in the sample S. The photodetector 30 may be selected appropriately according to detection conditions. Examples of photodetectors to be employed as the photodetector 30 include: CCD's, PD's (photodiodes); photomultipliers; and c-MOS's. In addition, the photodetector may be employed in combination with light dividing means, such as an optical filter or a spectroscope, according to detection conditions. Here, the optical filter 23 that cuts off the scattered light Lsa and transmits the fluorescence and the scattered light Lsb is provided between the two planoconvex lenses 24. Thereby, the fluorescence Lf can be efficiently detected while suppressing noise. That is, the fluorescence Lf can separated from the scattered light Lsa and detected. Note that in the first embodiment, the photodetector detects the fluorescence and the scattered light Lsb separately. Note that LAS-1000 manufactured by FUJIFILM Corporation is an example of an apparatus equipped with the optical system holding section 25, the two planoconvex lenses 24, the optical filter 23 and the photodetector 30, and can be favorably employed.

The correction calculating mechanism 40 estimates the intensity of the first electric field enhancing field Ewa from the relationship between the intensity of the first electric field enhancing field Ewa and the intensity of the second electric field enhancing field Ewb, using the scattered light Lsb, which is substantially proportionate to the intensity of the second electric field enhancing field and which is detected by the photodetector 30. The correction calculating mechanism 40 normalizes and corrects the intensity of fluorescence Lf with respect to the intensity of the first electric field enhancing field Ewa based on the estimated intensity of the first electric field enhancing field Ewa. A specific example of the correction calculating mechanism 40 is a personal computer. Note that the correction calculating mechanism 40 is not limited to being a personal computer, and may be any electronic calculator or the like, as long as the correction calculating mechanism serves the functions thereof.

Hereinafter, the fluorescence detecting method of the present invention will be described for a case in which the fluorescence detecting apparatus described above is employed to detect antigens A from within a sample S that includes the antigens A.

A case will be considered in which antigens A are detected from within a sample S that includes the antigens A as a detection target substance.

The fluorescence detecting method of the first embodiment utilizes antigen/antibody reactions to immobilize the fluorescent labels F onto the metal film 12. The reference light beam Lb is employed to perform total reflection measurement to detect the scattered light Lsb, and then the excitation light beam La is employed to perform total reflection measurement to detect the fluorescence Lf. The intensity of the scattered light Lsb is employed to correct the intensity of the fluorescence Lf.

In greater detail, the metal film 12 is modified with primary antibodies B1 that specifically bind with the antigens A. The sample S is caused to flow on the metal film 12, thereby causing the antigens and the primary antibodies B1 to specifically bind to each other. Then secondary antibodies B2, which are modified with fluorescent labels F and that also specifically bind with the antigens A, are caused to flow on the metal film 12. Thereby, the fluorescent labels F are immobilized to the metal film 12 via the specific bonds of the primary antibodies B1, the antigens A, and the secondary antibodies B2. Next, the reference light beam Lb emitted by the second light source 21b enters the interface between the dielectric plate 11 and the metal film 12 at a specific angle of incidence greater than or equal to a total reflection angle, to form the second electric field enhancing field Ewb within the sample on the metal film 12. The scattered light Lsb of the second electric field enhancing field Ewb is detected by the photodetector 30. The intensity of the scattered light Lsb is stored in the correction calculating mechanism 40. Thereafter, the excitation light beam La emitted by the first light source 21a is caused to enter the interface between the dielectric plate 11 and the metal film 12 at a specific angle of incidence greater than or equal to a total reflection angle, to form the first electric field enhancing field Ewa at the same location that the second electric field enhancing field was formed. The first electric field enhancing field Ewa excites the fluorescent labels F to cause the fluorescence Lf to be generated. The fluorescence Lf is detected by the photodetector 30, and the intensity of the fluorescence Lf is stored in the correction calculating mechanism 40. Then, the intensity of the first electric field enhancing field Ewa is estimated based on the relationship between the intensity of the first electric field enhancing field Ewa and the intensity of the second electric field enhancing field Ewb, using the intensity of the scattered light Lsb detected by the photodetector 30. Then, the intensity of the fluorescence Lf is normalized and corrected with respect to the intensity of the first electric field enhancing field Ewa.

In the case described above, the presence of the fluorescent labels F is actually directly confirmed by the detection of fluorescence. However, it is considered that the fluorescent labels F would not be immobilized onto the metal film 12 unless the antigens A are present. Therefore, the presence of the antigens A, is indirectly confirmed by confirming the presence of the fluorescent labels F.

The primary antibodies B1 are not particularly limited, and may be appropriately selected according to detection conditions (particularly according to the targets of detection). For example, in the case that the antigens A are CRP antigens (molecular weight: 110,000 Da), monoclonal antibodies (having different epitopes from the secondary antibodies B2 at least) that specifically bind with the antigens A may be employed as the primary antibodies B1. Known techniques may be employed to immobilize the primary antibodies B1 onto the metal film 12.

The fluorescent labels F are not particularly limited, as long as they emit the fluorescence Lf of a predetermined wavelength when excited by the excitation light beam La. The fluorescent labels F may be selected appropriately according to measurement conditions (such as the detection target substance and the wavelength of the excitation light beam). In the case that the wavelength of the excitation light beam La is approximately 650 nm, Cy5 pigment (fluorescence: 680 nm, fluorescence quantum yield: 0.3) may be employed, for example.

The electric field enhancing fields Ewa and Ewb are regions, which are formed locally on the upper surface of the metal film 12 by evanescent waves which are generated due to the excitation light beam La and the reference light beam Lb entering the interface between the dielectric plate 11 and the metal film 12 at specific angles of incidence greater than or equal to a total reflection angle, and by surface plasmon within the metal film 12 excited by the evanescent waves, that exhibit enhancing effects with respect to electric fields.

The excitation light beam La and the reference light beam Lb may be emitted separately or simultaneously. In the case that the excitation light beam La and the reference light beam Lb are emitted separately, because detection can be performed separately, only a single photodetector may be employed. On the other hand, in the case that the excitation light beam La and the reference light beam Lb are emitted simultaneously, it is necessary to employ two photodetectors, to avoid the fluorescence Lf and the scattered light Lsb from overlapping. Note that the first embodiment is an example of the former case, and the second embodiment to be described below is an example of the latter case.

Hereinafter, the operation and effects of the fluorescence detecting method and the fluorescence detecting apparatus of the first embodiment will be described.

In the fluorescence detecting method, the fluorescent labels F are present within the first electric field enhancing field Ewa. The fluorescent labels F are excited by the excitation effect of the first electric field enhancing field and caused to emit the fluorescence Lf. In theory, it is possible to calculate the amount of the detection target substance present in the sample S using the intensity of the fluorescence. However, margins of error in the shapes and settings of sensor chips; shifting in the incident angle of excitation light beams caused by human error such as margins of errors in sensing and margins of error in setup of the optical system; and shifting in surface plasmon generating conditions due to physical factors such as the refractive indices of samples, the refractive indices of the sensor chips, irregularities on the surfaces of the sensor chips, the thicknesses of the metal films, and the densities of the metal films, cause fluctuations to occur in the intensity of the first electric field enhancing field Ewa. Accordingly, correction becomes necessary.

Therefore, the fluorescence detecting method of the present invention employs the scattered light Ls of the second electric field enhancing field Ewb, which is generated due to irregularities in the surface of the dielectric plate 11 and the surface of the metal film 12, to correct the intensity of fluorescence. The correction is performed by: estimating the intensity of the first electric field enhancing field Ewa based on the relationship between the intensity of the first electric field enhancing field Ewa and the intensity of the second electric field enhancing field Ewb, using the intensity of the scattered light Lsb, which is substantially proportionate to the intensity of the second electric field enhancing field Ewb; and normalizing the intensity of fluorescence Lf with respect to the intensity of the first electric field enhancing field Ewa.

This correction is possible, because the percentage of light which is scattered at the first electric field enhancing field Ewa and the second electric field enhancing field Ewb does not vary due to the aforementioned shifts in the angles of incidence of the excitation light beam La and the reference light beam Lb, or the shifts in the surface plasmon generating conditions. Further, the intensity of the scattered light Lsb is substantially proportionate to the intensity of the second electric field enhancing field Ewb, and there is a relationship between the intensity of the first electric field enhancing field Ewa and the second electric field enhancing field Ewb. Therefore, the intensity of the scattered light Lsb serves as an index for estimating the intensity of the first electric field enhancing field Ewa.

Hereinafter, specific examples of calculations employed in the correcting method will be described.

Figure 2:
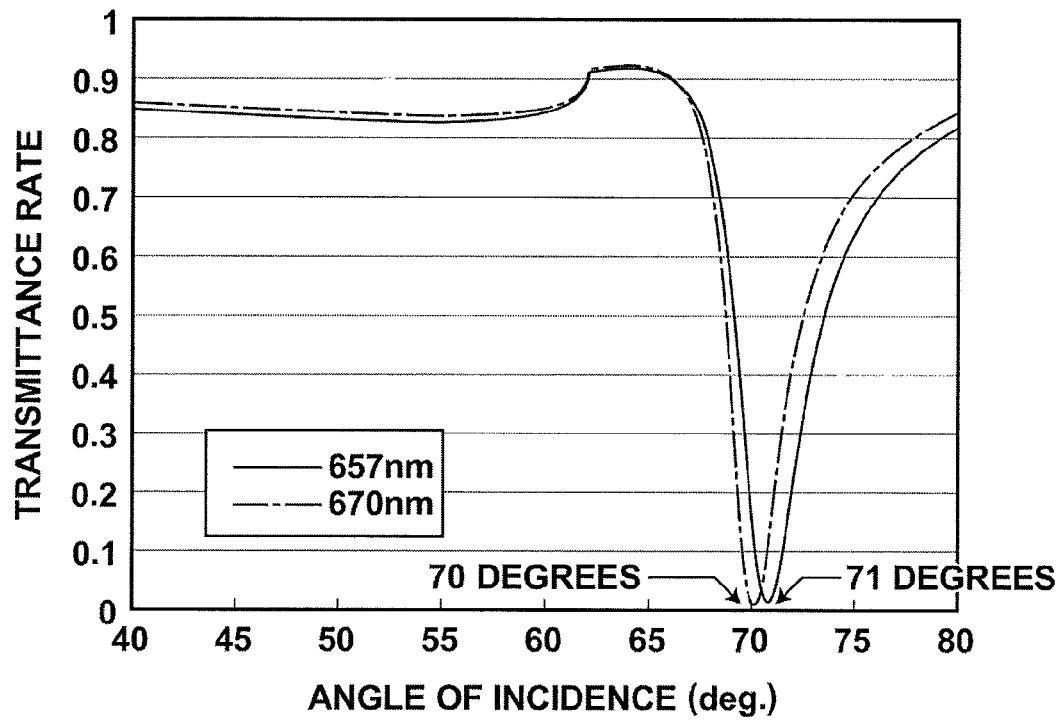
FIG. 2 is a graph that illustrates the relationships between angles of incidence and SPR reflection dips during total reflection measurement of a sample, using incident light beams having wavelengths of 657 nm and 670 nm.

FIG. 2 is a graph that illustrates the relationships between angles of incidence and SPR reflection dips during total reflection measurement of a sample, using incident light beams having wavelengths of 657 nm and 670 nm. The reflectance decreases at the positions of the SPR reflection dips, that is, the resonance angle at which surface plasmon is excited, because the energy of the incident light beams are absorbed in order to excite the surface plasmon. In other words, the intensity of the electric field enhancing field on the metal film 12 decreases at angles which are shifted from the resonance angle.

The reflectances of the light beams change in substantially the same manner, as illustrated in FIG. 2. Therefore, it is understood that the intensities of the first electric field enhancing field Ewa and the second electric field enhancing field Ewa also change in similar manners.

Here, the intensity of the scattered light Lsb changes because the intensity of the second electric field enhancing field, which generates the scattered light Lsb, changes. Generally, light sources, optical systems and the like are not moved at each measurement. Therefore, it is considered that changes in the intensities of electric field enhancing fields are caused by margins of error in the shapes and settings of sensor chips, shifting in the incident angle of excitation light beams caused by human error such as margins of errors in sensing and margins of error in setup of the optical system.

Accordingly, if the intensity of the scattered light Lsb decreases by ½, it can be understood that the intensity of the second electric field enhancing field Ewb has decreased by ½. If the intensity of the second electric field enhancing field Ewb decreases by ½, it can be understood that the intensity of the first electric field enhancing field Ewa. If the intensity of the first electric field enhancing field Ewa decreases by ½, it can be understood that the intensity of the fluorescence Lf has decreased by ½. That is, the following formula (I) can be employed to correct the intensity of fluorescence which is obtained at each measurement.

$$Ifc = If/Isb \tag{1}$$

wherein Ifc is the corrected intensity of fluorescence, If is the actual measured value of the intensity of fluorescence, and Isb is the actual measured value of the intensity of the scattered light Lsb of the second electric field enhancing field Ewb.

In the first embodiment, the reference light beam Lb, which has a wavelength longer than the wavelength of the excitation light beam La, is employed. In this case, the reference light beam Lb is capable of being transmitted through the optical filter 23 for separating the excitation light beam La and the fluorescence Lf. Therefore, measurements can be performed following obtainment of data for correction, without changing the optical system. In addition, only a single light receiving element, such as the photodetector 30, is necessary for this reason. Thereby, the intensity of fluorescence can be corrected by an extremely simple method.

Figure 3:
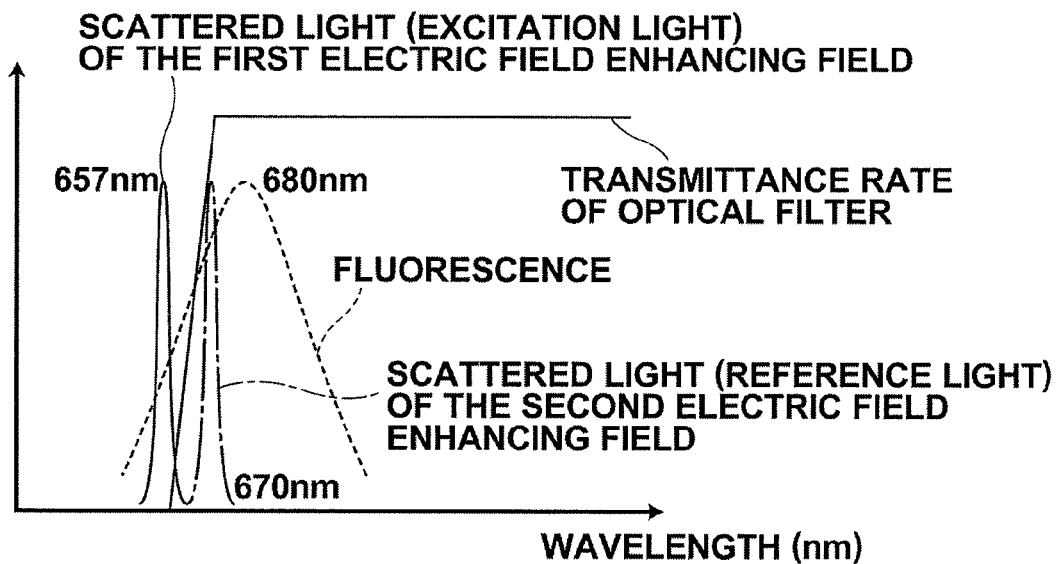
FIG. 3 is a graph that illustrates the relationships among the spectra of an excitation light beam (wavelength: 657 nm), a reference light beam (wavelength: 670 nm), fluorescence, and the transmittance rates of an optical filter.

In the first embodiment, the excitation light beam La and the reference light beam Lb are emitted separately. This is because the reference light beam Lb has a wavelength comparatively close to that of the wavelength of the excitation light beam. Therefore, the excitation light beam La and the reference light beam Lb are emitted separately, in order to enable effective separation of the scattered light Lsb of the second electric field enhancing field, and the fluorescence Lf. For example, in the case that Cy5 pigment (fluorescence: 680 nm, fluorescence quantum yield: 0.3) is employed as the fluorescent labels F in the first embodiment, the relationship among the spectra of the scattered light Lsa (the excitation light beam La) of the first electric field enhancing field Ewa, the scattered light Lsb (the reference light beam Lb) of the second electric field enhancing field Ewb, and the fluorescence are as illustrated in FIG. 3. Note that a portion of the scattered light Lsb is absorbed by the optical filter in a case such as that illustrated in FIG. 3. However, the intensity of the scattered light Lsb is generally greater than that of the fluorescence Lf by two or more orders of 10. Therefore, detection of the scattered light Lsb can be sufficiently performed, as long as 70% to 80% of the scattered light Lsb is transmitted through the optical filter.

As described above, factors that cause fluctuations in intensities of electric field enhancing fields that occur at each measurement are suppressed. Therefore, measurements having reproducibility can be realized simply and at low cost, without selecting or exchanging optimal components for each measurement.

Second Embodiment

A second embodiment of the present invention differs from the first embodiment only in that the wavelength of a reference light beam Lb is 780 nm, an excitation light beam La and the reference light beam Lb are emitted simultaneously, and two photodetectors are employed. Accordingly, descriptions of components of the second embodiment which are the same as those of the first embodiment will be omitted insofar as they are not particularly necessary.

Figure 4:
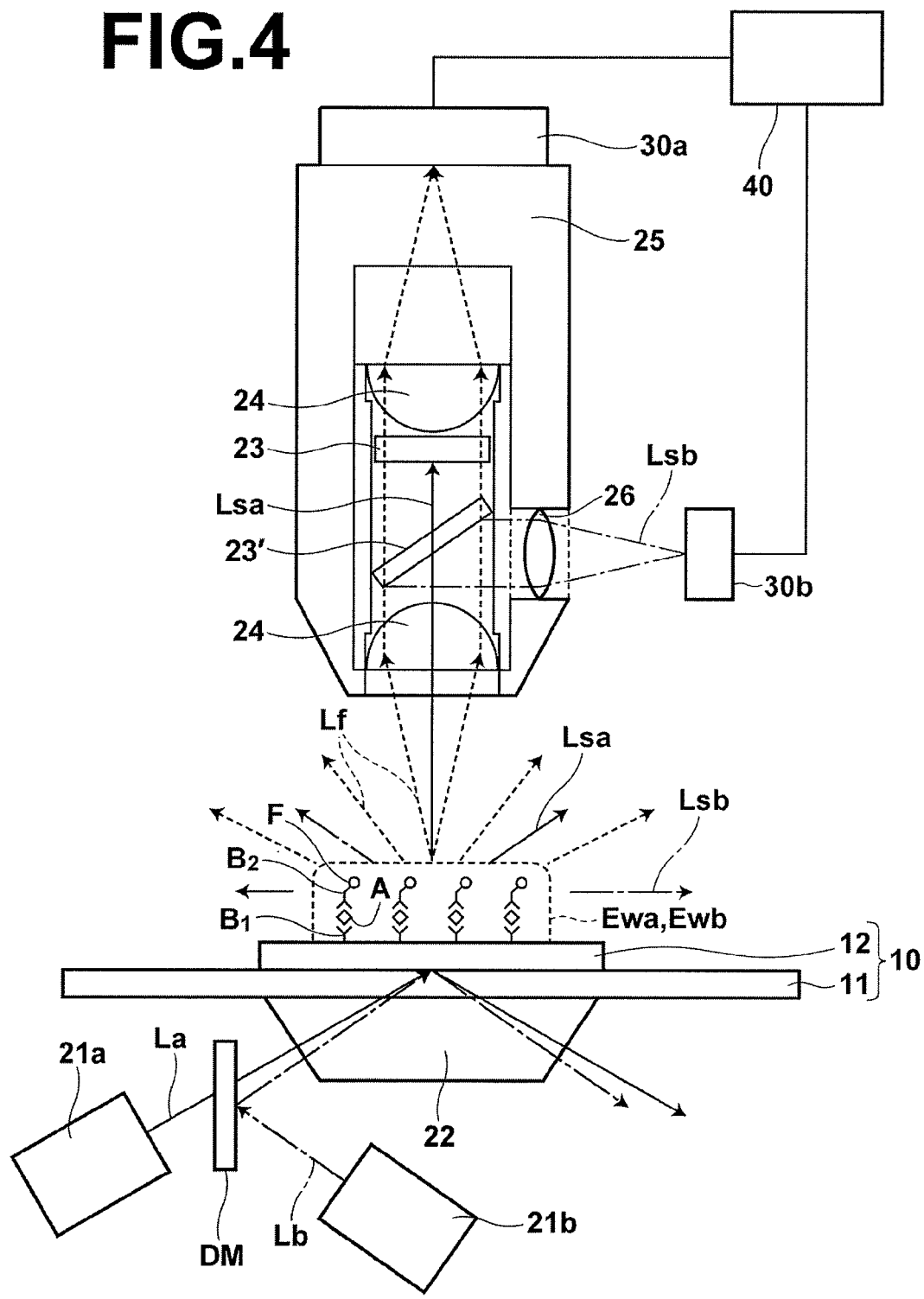
FIG. 4 is a schematic sectional view that illustrates a fluorescence detecting apparatus according to a second embodiment of the present invention.

As illustrated in FIG. 4, a fluorescence detecting apparatus according to the second embodiment of the present invention is the fluorescence detecting apparatus according to the first embodiment illustrated in FIG. 1, with a dichroic mirror 23' provided between the two planoconvex lenses 24 and toward the side of the optical filter 23 from which light enters, and a second photodetector 30b. Note that the second photodetector 30b is connected to the correction calculating mechanism 40 so as to transmit detected light signals thereto, in a similar manner as the photodetector 30 of the first embodiment (referred to as "first photodetector 30" in the second embodiment). The second photodetector 30b is provided to detect light which is reflected by the dichroic mirror 23'.

The dichroic mirror 23' reflects scattered light Lsb of a second electric field enhancing field Ewb, and transmits fluorescence Lf and scattered light Lsa of a first electric field enhancing field Ewa. Note that as illustrated in FIG. 4, a focusing lens 26 may be employed to focus the scattered light Lsb reflected by the dichroic mirror 23' onto the second photodetector 30b. Note that a diffraction grating or the like may be employed instead of the dichroic mirror 23'.

The photodetector 30b is not particularly limited, and a photodetector similar to that which is used as the first photodetector 30a (photodetector 30) may be employed. The second photodetector 30b may be provided outside the optical system holding section 25 or built into the optical system holding section 25.

The wavelength of the reference light beam Lb is not particularly limited. However, it is necessary to consider the fact that the spectra of the fluorescence Lf and the scattered light Lsb may overlap in the second embodiment. Therefore, it is preferable for the wavelength of the reference light beam Lb to be sufficiently long enough to enable separation of the fluorescence Lf and the scattered light Lsb.

In the fluorescence detecting method of the second embodiment, fluorescent labels F are immobilized onto a metal plate 12 in the same manner as in the first embodiment. Next, the excitation light beam La and the reference light beam Lb emitted by the first light source 21a and the second light source 21b enter the interface between the dielectric plate 11 and the metal film 12 at specific angles of incidence greater than or equal to a total reflection angle simultaneously, to form the first electric field enhancing field Ewa and the second electric field enhancing field Ewb within the sample on the metal film 12. The scattered light Lsb of the second electric field enhancing field Ewb is reflected by the dichroic mirror 23' and detected by the second photodetector 30b. The intensity of the scattered light Lsb is stored in the correction calculating mechanism 40. At the same time, the first electric field enhancing field Ewa excites the fluorescent labels F to cause the fluorescence Lf to be generated. The fluorescence Lf is detected by the first photodetector 30a, and the intensity of the fluorescence Lf is stored in the correction calculating mechanism 40. Next, the intensity of the first electric field enhancing field Ewa is estimated based on the relationship between the intensity of the first electric field enhancing field Ewa and the intensity of the second electric field enhancing field Ewb, using the intensity of the scattered light Lsb detected by the photodetector 30. Then, the intensity of the fluorescence Lf is normalized and corrected with respect to the intensity of the first electric field enhancing field Ewa.

Hereinafter, the operations and effects of the fluorescence detecting method and the fluorescence detecting apparatus of the second embodiment will be described.

In the second embodiment, there is a great difference between the wavelength of the excitation light beam La (657 nm) and the wavelength of the reference light beam Lb (780 nm). Therefore, the relationship between the intensity of the first electric field enhancing field Ewa and the intensity of the second electric field enhancing field Ewb is slightly more complex. However, it is possible to estimate the intensity of the first electric field enhancing field Ewa based on the relationship between the intensity of the first electric field enhancing field Ewa and the intensity of the second electric field enhancing field Ewb, using the intensity of the scattered light Lsb, which is substantially proportionate to the intensity of the second electric field enhancing field Ewb. Therefore, it is also possible to normalize the intensity of fluorescence Lf with respect to the intensity of the first electric field enhancing field Ewa.

Figure 5:
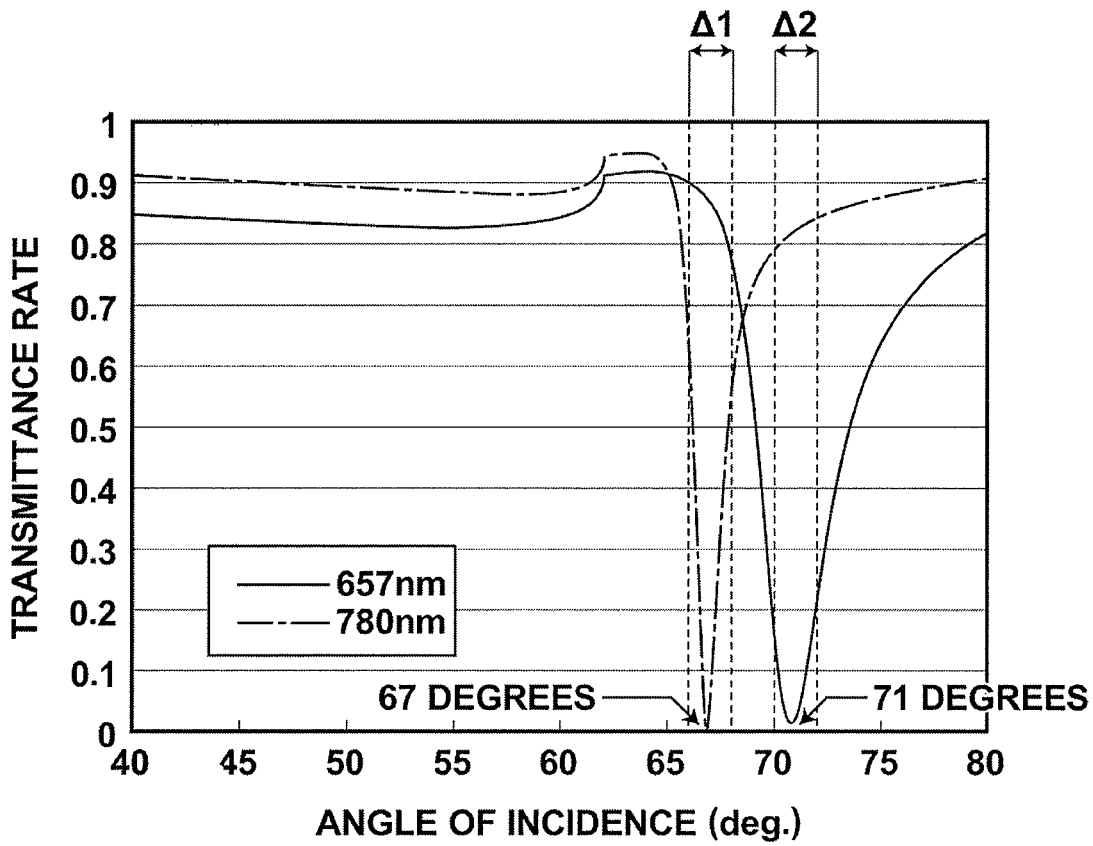
FIG. 5 is a graph that illustrates the relationships between angles of incidence and SPR reflection dips during total reflection measurement of a sample, using incident light beams having wavelengths of 657 nm and 780 nm.

FIG. 5 is a graph that illustrates the relationships between angles of incidence and SPR reflection dips during total reflection measurement of a sample, using an excitation light beam La (wavelength: 657 nm) and a reference light beam Lb (wavelength: 780 nm). As illustrated in FIG. 5, the changes in the SPR reflection dips differ greatly. Therefore, it can be understood that the intensities of the first electric field enhancing field Ewa and the second electric field enhancing field Ewb will differ greatly for given shifts in the angles of incidence of light beams.

In this case, it can be seen that in cases that shifts of ±1 degree occur (Δ1 and Δ2 illustrated in FIG. 5) in the angles of incidence of the excitation light beam La and the reference light beam Lb from optimal surface plasmon conditions (the resonance angles), the reflectance of the excitation light beam La changes within a range from approximately 0 to 0.2, while the reflectance of the reference light beam Lb changes within a range from approximately 0 to 0.6. For example, the reflectances of the excitation light beam La and the reference light beam Lb are 0.2 and 0.6 at points on the graph ±1 degree shifted from the resonance angle. Therefore, the intensity of the first electric field enhancing field Ewa decreases by approximately 80%, and the intensity of the second electric field enhancing field Ewb decreases by approximately 40%.

In this manner, there is a relationship between the intensity of the first electric field enhancing field Ewa and the intensity of the second electric field enhancing field Ewb. Therefore, if the relationship is obtained in advance, and employed as calibrating data, the intensity of the fluorescence Lf emitted by the fluorescent labels F can be normalized and corrected with respect to the intensity of the first electric field enhancing field Ewa.

As described above, factors that cause fluctuations in intensities of electric field enhancing fields that occur at each measurement are suppressed. Therefore, the same advantageous effects as those obtained by the first embodiment can also be obtained by the second embodiment.

Figure 6:
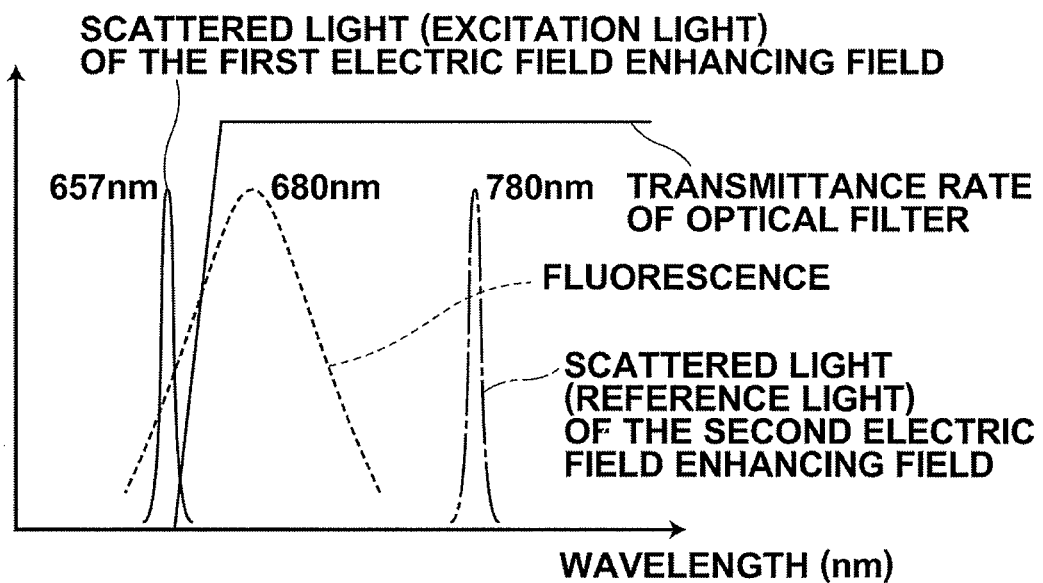
FIG. 6 is a graph that illustrates the relationships among the spectra of an excitation light beam (wavelength: 657 nm), a reference light beam (wavelength: 780 nm), fluorescence, and the transmittance rates of an optical filter.
Figure 7:
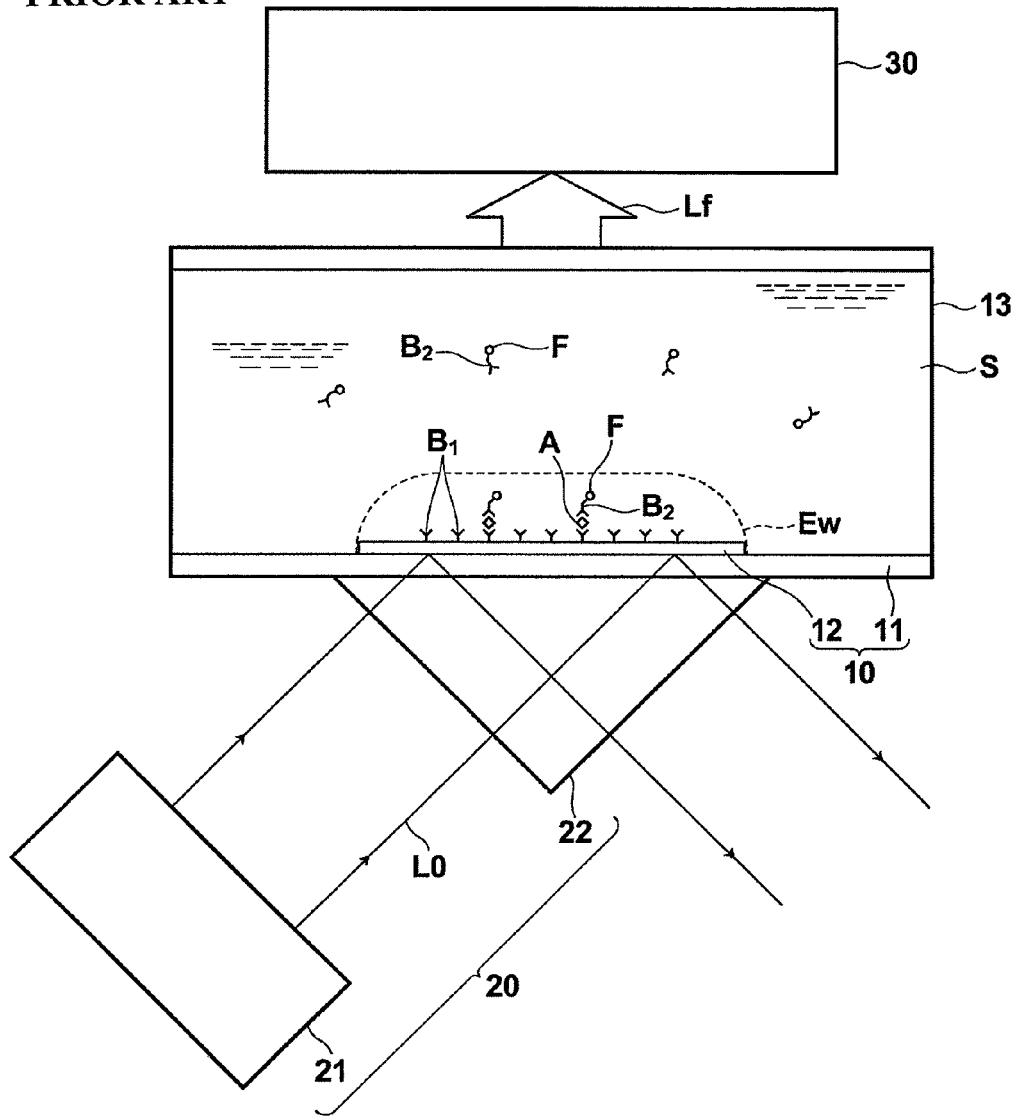
FIG. 7 is a schematic sectional view that illustrates a conventional fluorescence detecting apparatus.

In addition, in the second embodiment, the excitation light beams La and the reference light beam Lb can be emitted simultaneously. Therefore, the time required to perform measurements can be shortened, and measurements can be performed more efficiently. For example, in the case that Cy5 pigment (fluorescence: 680 nm, fluorescence quantum yield: 0.3) is employed as the fluorescent labels F in the first embodiment, the relationship among the spectra of the scattered light Lsa (the excitation light beam La) of the first electric field enhancing field Ewa, the scattered light Lsb (the reference light beam Lb) of the second electric field enhancing field Ewb, and the fluorescence are as illustrated in FIG. 6.

As described above, the present invention suppresses factors that cause fluctuations in intensities of electric field enhancing fields that occur at each measurement. Therefore, measurements having reproducibility can be realized simply and at low cost, without selecting or exchanging optimal components for each measurement.

What is claimed is:

1. A fluorescence detecting method, comprising the steps of:
preparing a dielectric plate, and a metal film which is provided at a predetermined region on one surface of the dielectric plate, onto which a sample that includes a detection target substance and fluorescent labels is supplied;
irradiating an excitation light beam through the dielectric plate such that it enters the interface between the dielectric plate and the metal film, to cause a first electric field enhancing field to be generated on the surface of the metal film;
detecting fluorescence emitted by the fluorescent labels due to excitation by the first electric field enhancing field with a first photodetector;
detecting the amount of the detection target substance based on the intensity of fluorescence detected by the first photodetector;
irradiating a reference light beam having a longer wavelength than the excitation light beam through the dielectric plate, to cause a second electric field enhancing field to be generated on the surface of the metal film at the same location as the first electric field enhancing field;
detecting scattered light of the second electric field enhancing field, which is substantially proportionate to the intensity of the second electric field enhancing field, with a second photodetector;
estimating the intensity of the first electric field enhancing field based on the relationship between the intensity of the first electric field enhancing field and the intensity of the second electric field enhancing field, using the intensity of the scattered light detected by the second photodetector; and
normalizing and correcting the intensity of fluorescence with respect to the intensity of the first electric field enhancing field.

2. A fluorescence detecting method as defined in claim 1, wherein:
the excitation light beam and the reference light beam are irradiated simultaneously.

3. A fluorescence detecting apparatus, for detecting the amount of a detection target substance, comprising:
a dielectric plate;
a metal film which is provided at a predetermined region on one surface of the dielectric plate, onto which a sample that includes the detection target substance and fluorescent labels is supplied;
a light source for irradiating an excitation light beam through the dielectric plate such that it enters the interface between the dielectric plate and the metal film, to cause an electric field enhancing field to be generated on the surface of the metal film;
a first photodetector for detecting the intensity of fluorescence generated by the excitation effect of the electric field enhancing field;
a light source for irradiating a reference light beam having a longer wavelength than the excitation light beam through the dielectric plate, to cause a second electric field enhancing field to be generated on the surface of the metal film at the same location as the first electric field enhancing field;
a second photodetector for detecting scattered light of the second electric field enhancing field, which is substantially proportionate to the intensity of the second electric field enhancing field; and
a correcting mechanism, for normalizing and correcting the intensity of fluorescence with respect to the intensity of the first electric field enhancing field based on the relationship between the intensity of the first electric field enhancing field and the intensity of the second electric field enhancing field, using the intensity of the scattered light detected by the second photodetector;
the amount of the detection target substance being detected based on the intensity of fluorescence detected by the first photodetector, which has been corrected by the correcting mechanism.

4. A fluorescence detecting method, comprising the steps of:
preparing a dielectric plate, and a metal film which is provided at a predetermined region on one surface of the dielectric plate, onto which a sample that includes a detection target substance and fluorescent labels is supplied;
irradiating an excitation light beam through the dielectric plate such that it enters the interface between the dielectric plate and the metal film, to cause a first electric field enhancing field to be generated on the surface of the metal film;

detecting fluorescence emitted by the fluorescent labels due to excitation by the first electric field enhancing field with a first photodetector;

detecting the amount of the detection target substance based on the intensity of fluorescence detected by the first photodetector;

irradiating a reference light beam having a longer wavelength than the excitation light beam through the dielectric plate, to cause a second electric field enhancing field to be generated on the surface of the metal film at the same location as the first electric field enhancing field;

detecting scattered light of the second electric field enhancing field, which is substantially proportionate to the intensity of the second electric field enhancing field, with the first photodetector;

estimating the intensity of the first electric field enhancing field based on the relationship between the intensity of the first electric field enhancing field and the intensity of the second electric field enhancing field, using the intensity of the scattered light detected by the first photodetector; and normalizing and correcting the intensity of fluorescence with respect to the intensity of the first electric field enhancing field, wherein the excitation light beam and the reference light beam are irradiated separately.

5. A fluorescence detecting apparatus for detecting the amount of a detection target substance, comprising:

a dielectric plate;

a metal film which is provided at a predetermined region on one surface of the dielectric plate, onto which a sample that includes the detection target substance and fluorescent labels is supplied;

a light source for irradiating an excitation light beam through the dielectric plate such that it enters the interface between the dielectric plate and the metal film, to cause an electric field enhancing field to be generated on the surface of the metal film;

a first photodetector for detecting the intensity of fluorescence generated by the excitation effect of the electric field enhancing field;

a light source for irradiating a reference light beam having a longer wavelength than the excitation light beam through the dielectric plate, to cause a second electric field enhancing field to be generated on the surface of the metal film at the same location as the first electric field enhancing field, the first photodetector detecting scattered light of the second electric field enhancing field, which is substantially proportionate to the intensity of the second electric field enhancing field; and a correcting mechanism, for normalizing and correcting the intensity of fluorescence with respect to the intensity of the first electric field enhancing field based on the relationship between the intensity of the first electric field enhancing field and the intensity of the second electric field enhancing field, using the intensity of the scattered light detected by the first photodetector;

the amount of the detection target substance being detected based on the intensity of fluorescence detected by the first photodetector, which has been corrected by the correcting mechanism.

* * * * *